United States Patent [19]

Töpfl

[11] Patent Number: 4,740,236
[45] Date of Patent: Apr. 26, 1988

[54] N-SULFONYL-IMINO-THIOCARBONIC ACID DIESTERS AS HERBICIDE ANTAGONISTS FOR THE PROTECTION OF RICE CROPS

[75] Inventor: Werner Töpfl, Dornach, Switzerland

[73] Assignee: Ciba-Geigy Corporation, Ardsley, N.Y.

[21] Appl. No.: 554,734

[22] Filed: Nov. 23, 1983

[30] Foreign Application Priority Data

Dec. 3, 1982 [CH] Switzerland ............... 7048/82

[51] Int. Cl.$^4$ ............................................. A01N 41/10
[52] U.S. Cl. .......................................... 71/103; 71/100
[58] Field of Search ........................ 71/100, 103, 118

[56] References Cited

U.S. PATENT DOCUMENTS

| 3,133,810 | 5/1964 | Hamm | 71/101 |
| 3,268,539 | 8/1966 | Levy | 260/453 RW |
| 3,318,681 | 5/1967 | Yates | 260/453 RW |
| 3,649,664 | 3/1972 | Richter et al. | 260/453 RW |
| 3,933,894 | 1/1976 | Stephens | 71/103 |
| 4,231,786 | 11/1986 | Czajkowski et al. | 71/100 |
| 4,297,295 | 10/1981 | Ganghan et al. | 71/100 |
| 4,317,310 | 3/1982 | Bollinger | 47/57.6 |
| 4,433,997 | 2/1984 | Pallos | 71/100 |
| 4,441,916 | 4/1984 | Baker et al. | 71/100 |

OTHER PUBLICATIONS

Gompper et al., "N-Sulfonyl-Iminodithiokohlensäure Ester und N-Sulfonyl-Dithiourethane", Chemische Berichte 99, 2885 (1966).

Primary Examiner—Richard L. Raymond
Assistant Examiner—Susan Treanor
Attorney, Agent, or Firm—Edward McC. Roberts; Bruce M. Collins

[57] ABSTRACT

N-Sulfonyliminothiocarbonic acid diesters protect rice crops from phytotoxic damage caused by herbicides.

25 Claims, No Drawings

N-SULFONYL-IMINO-THIOCARBONIC ACID DIESTERS AS HERBICIDE ANTAGONISTS FOR THE PROTECTION OF RICE CROPS

The present invention relates to N-sulfonyl-imino-thiocarbonic acid diesters which are suitable as herbicide antagonists for the protection of rice crops from phytotoxic damage caused by herbicides. The N-sulfonyl-imino-thiocarbonic acid diesters are applied to the cultivated crops either simultaneously with, or shortly after, the application of the herbicide. There can also be used a composition containing both the herbicide and the N-sulfonyl-imino-thiocarbonic acid diester; or the seeds of the cultivated plants can be pretreated (dressed) with the N-sulfonyl-imino-thiocarbonic acid diester, and the sown or emerged crops subsequently treated with the herbicide. The invention relates also to compositions containing the N-sulfonyl-imino-thiocarbonic acid diesters, and also to the use thereof.

It is known that herbicides of the most varied classes of substances, such as triazines, urea derivatives, carbamates, thiolcarbamates, haloacetanilides, halophenoxyacetic acid, and so forth, can, when applied in effective amounts, sometimes damage to some degree the cultivated plants besides acting against the weeds to be controlled. Overdoses are often accidently applied along boundary areas when spraying is being carried out in strips, either as a result of the action of the wind or as a result of a wrong estimation of the spread effect of the spraying device being used. Climatic conditions and the nature of the soil can also play a part, so that the amount of herbicide recommended for normal conditions has the effect of an overdose. Furthermore, the quality of the seed with respect to its compatibility with the herbicide is also a factor to be taken account of. With the aim of overcoming this problem, there have already been suggested various substances which are capable of specifically antagonising the harmful action of a herbicide on the cultivated plants, that is to say, capable of protecting the cultivated plants without at the same time noticeably affecting the herbicidal action against the weeds to be controlled. It has however been shown that the suggested antidotes frequently have only a narrow field of action, both with respect to the cultivated plants and to the herbicide, and also with respect to the dependence of their action in some cases on the mode of their application, in other words, a specific antidote is suitable often for only a certain variety of cultivated plant and for only a few classes of herbicidal substances.

The N-sulfonyl-imino-thiocarbonic acid diesters of the present invention correspond to the formula I

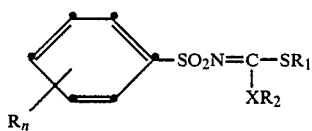

wherein
n is zero, 1, 2 or 3,
R is halogen, cyano, nitro, a radical $-Y-C_1-C_4$-alkyl, $-Y-C_3-C_6$-alkenyl, $-Y-C_3-C_6$-alkynyl, $-Y$-phenyl or $-Y$-aralkyl, each unsubstituted or substituted by halogen, cyano, nitro, $C_1-C_4$-alkoxy, $C_1-C_4$-alkoxycarbonyl, carbamoyl, sulfamoyl, $C_1-C_4$-mono- or dialkylcarbamoyl, $C_1-C_4$-mono- or dialkylsulfamoyl, or is a radical $-COOR_3$, $-NR_3R_4$, $-CONR_3R_4$, $-NHCONR_3R_4$ or $-SO_2NR_3R_4$, or two adjacent R's together form a 3–4-membered, saturated or unsaturated hydrocarbon chain, the chain members of which can be replaced once by oxygen or sulfur and/or once to three times by nitrogen, $R_1$ and $R_2$ independently of one another are each a $C_1-C_4$-alkyl, $C_3-C_6$-alkenyl, $C_3-C_6$-alkynyl, phenyl or aralkyl group, which can be unsubstituted or substituted by halogen, cyano, nitro, $C_1-C_4$-alkyl, $C_1-C_4$-haloalkyl or $C_1-C_4$-alkoxy, or one of $R_1$ and $R_2$ can also be hydrogen or can form a 5- or 6-membered, saturated or unsaturated heterocycle which is bound by way of a carbon atom, contains 1–3 hetero atoms and can also be annularly-linked to a benzene ring, and which can be substituted by halogen and/or methyl, $R_3$ is a $C_1-C_4$-alkyl, $C_3-C_6$-alkenyl, $C_3-C_6$-alkynyl or $C_3-C_6$-cycloalkenyl group, each of which can be substituted by halogen, cyano, nitro or $C_1-C_4$-alkyl, $R_4$ is hydrogen, the same as $R_3$, or a phenyl or aralkyl group which can be substituted by halogen, cyano, nitro, $C_1-C_4$-alkyl, $C_1-C_4$-haloalkyl or $C_1-C_4$-alkoxy, or $R_3$ and $R_4$ together with the nitrogen atom to which they are bound form a 5- or 6-membered, saturated or unsaturated heterocycle which can also contain oxygen, sulfur, nitrogen or a methylimino group as ring member, X is oxygen or sulfur, and
Y is the direct bond or an oxygen, sulfur, sulfinyl, sulfonyl, imino or methylimino bridge.

The term 'alkyl' on its own or as part of a substituent embraces both branched-chain and straight-chain alkyl groups, which contain the given number of carbon atoms. Examples are: methyl, ethyl, propyl, isopropyl, butyl, isobutyl, sec-butyl or tert-butyl. Correspondingly, the alkenyl and alkynyl groups can be straight-chain or branched-chain.

Aralkyl groups contain 1–4 carbon atoms in the alkyl moiety, while the aryl group can be naphthyl or preferably phenyl. Benzyl and phenylethyl are the preferred aralkyl groups.

The alkenyl and alkynyl groups contain 3–6 carbon atoms, they can be branched-chain or straight-chain and can contain one or two unsaturated positions. Examples are: allyl, methallyl, butenyl, butadienyl, pentenyl or hexenyl, propargyl, butyne, pentyne and hexyne.

Cycloalkyl groups in the present case are cyclopropyl, cyclobutyl, cyclopentyl and cyclohexyl. Heyterocycles can be 5- or 6-membered and are saturated or unsaturated. The heterocycles formed by $R_3$ and $R_4$ are bound by way of nitrogen; the others formed by $R_1$ and $R_2$ are bound by way of carbon. Examples are: pyrrole, pyrolidine, imidazole, pyrazole, pyridine, piperidine, pyrimidine, pyridazine, oxazole, oxazoline, oxazolidine, thiazole, thiazolidine, oxadiazole, thiadiazole, morpholine and pyrazole rings. The symbols $R_1$ and $R_2$ can also denote thiophene, furan tetrahydrofuran or pyran. Heterocycles annularly-linked to a benzene ring, which are formed by two R's with the phenyl ring $R_1$ and $R_2$, are for example benzothiophene, benzothiazole, benzoxazole, indole, isoindole, indazole, isoquinoline and quinoline.

Halogen is in particular fluorine, chromium and bromine, in some cases also iodine.

A good protective action is obtained with the N-sulfonyl-amino-thiocarbonic acid diesters of the formula I wherein
one or both X symbols are sulfur;
X is sulfur, and n is 1 or 2;
X is sulfur, n is 1 or 2, and the radical R is in the meta or para-position with respect to the sulfonylimino group;
X is sulfur, n is 1 or 2, and R is halogen and optionally $C_1$-$C_4$-alkyl, $C_1$-$C_4$-haloalkyl, $C_1$-$C_4$-haloalkoxy, cyano or nitro; and
X is sulfur, and $R_1$ and $R_2$ are each methyl.

To be emphasised by virtue of their good protective action are: the N-(4-chlorobenzenesulfonyl)-imino-dithiocarbonic acid dimethyl ester; the N-(4-bromobenzenesulfonyl)-imino-dithiocarbonic acid dimethyl ester; and the N-(3,4-dichlorobenzenesulfonyl)-imino-dithiocarbonic acid dimethyl ester.

The N-sulfonyliminothiocarbonic acid diesters of the formula I are excellently suitable for protecting rice crops against the phytotoxic action of herbicides of the most varied classes of substances, such as: triazines, phenylurea derivatives, carbamates, thiolcarbamates, haloacetanilides, halophenoxyacetic acid esters, substituted phenoxyphenoxyacetic acid esters and -propionic acid esters, substituted pyridineoxyphenoxyacetic acid esters and -propionic acid esters, benzoic acid derivatives, and so forth, in so far as these are not selective or not sufficiently selective in their action, that is, they cause damage to a greater or lesser extent to the rice plants besides attacking the weeds to be controlled. The invention relates also to compositions which contain the N-sulfonyl-imino-thiocarbonic acid diesters of the formula I together with herbicides.

There have already been suggested, as antidotes, various substances which are able to specifically antagonise the harmful action of a herbicide on the cultivated plants, that is to say, able to protect the cultivated plants without at the same time to noticeably reduce the herbicidal action against the weeds to be controlled. Depending on its properties, an antidote of this type. Known also as 'safener', can be used for the pretreatment of the seed of the cultivated plant (dressing of the seed or seedlings), or can be introduced into the seed furrows before sowing, or can be used as a tank mixture together with the herbicide, before or after the emergence of the plants.

The G.B. Patent Specification No. 1,277,557 describes for instance the treatment of seeds or shoots of wheat and millet with certain oxamic acid esters and amides for protection against an attack by N-methoxymethyl-2',6'-diethyl-chloroacetanilide (Alachlor). In other publications (German Offenlegungsschriften Nos. 1,952,910 and 2,245,471 and French Patent Specification No. 2,021,611), there are suggested antidotes for the treatment of the seeds of cereals, maize and rice to protect them against the attack by herbicidal thiolcarbamates. In the German Patent Specification No. 1,567,075 and in the U.S. Pat. No. 3,131,509, hydroxyamino-acetanilides and hydantoins are suggested for the protection of cereal seed against carbamates, such as IPC, CIPC, and so forth. In the U.S. Pat. No. 4,317,310, there are recommended 2-imino-1,3-thiolanes, -1,3-dithiols, -1,3-dithianes, -1,3-dithiethanes and -1,3-oxathiazoles for protecting rice crops against the action of chloroacetanilide and thiocarbamate herbicides. In further development, however, all these preparations have proved inadequate.

The N-sulfonyl-imino-thiocarbonic acid diesters of the formula I surprisingly have the property of being able to protect rice plants against attack by aggressive agricultural chemicals, particularly herbicides of the most varied classes of substances, for example chloroacetanilides, chloroacetamides, carbamates and thiocarbamates, diphenyl ethers and nitrodiphenyl ethers, benzoic acid derivatives, triazines and triazinones, phenylureas, nitroanilines, oxdiazolones, pyridyloxyphenoxy derivatives, phosphates and pyrazoles, in cases where the herbicides are not tolerant or insufficiently tolerant towards cultivated plants.

The rice plants are protected by the N-sulfonyliminothiocarbonic acid diesters according to the present invention particularly against the herbicides of the following classes: chloroacetanilides, chloroacetamides, thiocarbamates and phosphates.

Depending on the purpose of application, such an antidote of the formula I can be used for the pretreatment of the seed or seedlings of the cultivated plant (dressing of the seed or of cuttings), or can be introduced into the soil before or after sowing, or can be applied on its own or together with the herbicide before or after emergence of the plants. The treatment of the plant or of the seed or seedlings with the antidote can be carried out therefore essentially independently of the time of application of the phytotoxic chemical. It can however also be carried out simultaneously (tank mixture). The pre-emergence treatment includes both the treatment of the cultivated area before sowing (ppi="pre plant incorporation") and the treatment of the sown cultivated area before emergence of the plants.

The applied amounts of antidote in proportion to the herbicide depend largely on the mode of application. In the case of field treatment, which is carried out either with the use of a tank mixture or with a separate application of herbicide and antidote, the employed ratio of antidote to herbicide is a rule from 1:100 to 10:1, preferably however the range is 1:5 to 8:1, especially 1:1.

With seed dressing and similar specific protective measures, however, the amounts of antidote required compared with for example the amounts of herbicide which would be applied later per hectare of cultivated land are much smaller. There are used for seed dressing as a rule 0.1 to 10 g of antidote per kg of seed, the amount preferred being between 1 and 2 g. When the antidote is to be applied shortly before sowing, by seed soaking, there are preferably used for example antidote solutions containing the active ingredient at a concentration of 1–10,000 ppm, particularly 100–1000 ppm.

Protective measures such as seed dressing with an antidote of the formula I and possible subsequent field treatment with acricultural chemicals are as a rule separated by a considerable interval of time. Pretreated seed and plant material can come into contact later, in agriculture, horticulture and forestry, with various chemicals. The present invention relates therefore also to compositions for protecting rice plants, which compositions contain as active ingredient an antidote of the formula I together with customary carriers. These preparations can if required be additionally mixed with the herbicide against which the cultivated plant is to be protected.

The antidote of the invention is to be used in all cases where a cultivated plant has to be protected against the phytotoxicity of a chemical.

The following are for example listed as herbicides against the action of which the cultivated plants have to be protected:

chloroacetanilides: 2-chloro-2',6'-diethyl-N-(2''-propyloxyethyl)-acetanilide ("Pretilachlor"), 2-chloro-6'-ethyl-N-(2''-methoxy-1''-methylethyl)-acet-o-toluidide ("Metolachlor"), 2-chloro-2',6'-diethyl-N-(butoxymethyl)-acetanilide ("Butachlor"), 2-chloro-6'-ethyl-N-(ethoxymethyl)-acet-o-toluidide ("Acetochlor"), 2-chloro-6'-ethyl-N-(2''-propoxy-1''-methylethyl)-acet-o-toluidide, 2-chloro-2',6'-dimethyl-N-(2''-methoxy-1''-methylethyl)-acetanilide, 2-chloro-2',6'-dimethyl-N-(2''-methoxyethyl)-acetanilide ("Dimethachlor"), 2-chloro-2',6'-diethyl-N-(pyrazol-1-ylmethyl)-acetanilide, 2-chloro-6'-ethyl-N-(pyrazol-1-ylmethyl)-acet-o-toluidide, 2-chloro-6'-ethyl-N-(3,5-dimethyl-pyrazol-1-ylmethyl)-acet-o-toluidide, 2-chloro-6'-ethyl-N-(2''-butoxy-1''-methylethyl)-acet-o-toluidide ("Metazolachlor"), 2-chloro-6'-ethyl-N-(2''-butoxyl-1''-(methylethyl)-acet-o-toluidide, 2-chloro-2'-trimethylsilyl-N-(butoxymethyl)-acetanilide, 2-chloro-2',6'-diethyl-N-(methoxymethyl)-acetanilide ("Alachlor") and 2-chloro-2',6'-diethyl-N-(ethoxycarbonylmethyl)-acetanilide;

chloroacetamide: N-[1-isopropyl-2-methylpropen-1-yl(1)]-N-(2'-methoxyethyl)-chloroacetamide;

sulfonylureas: N-(2-chlorobenzenesulfonyl)-N'-(4-methoxy-6-methyl-1,3,5-triazinyl)-urea (DPX 4189), N-(2-chloroethylbenzenesulfonyl)-N-(4-methoxy-6-methyl-1,3,5-triazinyl)-urea and N-(2-methoxyethylbenzenesulfonyl)-N'-(4-methoxy-6-methyl-1,3,5-triazinyl)-urea;

carbamates and thiocarbamates: N-(3',4'-dichlorophenyl)-propionanilide ("Propanil"), S-4-chlorobenzyl-diethylthiocarbamate ("Thiobencarb"), S-ethyl-N,N-hexamethylene-thiocarbamate ("Molinate"), S-ethyl-dipropyl-thiocarbamate ("EPTC"), N,N-di-sec-butyl-S-benzyl-thiocarbamate (Drepamon), S-(2,3-dichloroallyl)-di-isopropylthiocarbamate and S-(2,3,3-trichloroallyl)-di-isopropylthiocarbamate (Di- and Tri-allate"), 1-(propylthiocarbonyl)-decahydro-quinaldine, S-4-benzyldiethylthiocarbamate, as well as corresponding sulfinylcarbamates;

diphenyl ethers and nitrodiphenyl ethers: 2,4-dichlorophenyl-4'-nitophenyl ether ("Nitrofen"), 2-chloro-1-(3'-ethoxy-4'-nitrophenoxy)-4-trifluoromethyl-benzene ("Oxyfluorfen"), 2',4'-dichlorophenyl-3-methoxy-4-nitrophenyl ether ("Chloromethoxinyl"), 2-[4'-(2'',4''-dichlorophenoxy)-phenoxy)-propionic acid methyl ester and N-(2'-methoxyethyl)-2-[5'-(2''-chloro-4''-trifluoromethylphenoxy)phenoxy]-propionic acid amide;

benzoic acid derivatives: methyl-5-(2',4'-dichlorophenoxy)-2-nitrobenzoate ("Bifenox"), 5-(2'-chloro-4'-trifluoromethylphenoxy)-2-nitrobenzoic acid ("Acifluorfen") and 2,6-dichlorobenzonitrile ("Dichlobenil");

triazines and triazinones: 2,4-bis(isopropylamino)-6-methylthio-1,3,5-triazine ("Prometryn"), 2,4-bis(ethylamino)-6-methylthio-1,3,5-triazine ("Simetryn"), 2-(1',2'-dimethylpropylamino)-4-ethylamino-6-methylthio-1,3,5-triazine ("Dimethametryn") and 4-amino-6-tert-butyl-4,5-dihydro-3-methylthio-1,2,4-triazin-5-one ("Metribuzin");

phenylureas: N-(3'-isopropylphenyl)-N',N'-dimethylurea ("Isoproturon"), N-(3',4'-dimethylbenzyl)-N'-4-tolylurea ("Dimuron") and N-(3'-chloro-4'-isopropylenyl)-N',N'-(3methyl-pentamethylen-1,5-yl)-urea;

nitroanilines: 2,6-dinitro-N,N-dipropyl-4-trifluoromethylaniline ("Trifluralin") and N-(1'-ethylpropyl)-2,6-dinitro-3,4-xylinine ("Pendimethalin");

oxadiazolones: 5-tert-butyl-3-(2',4'-dichloro-5'-isopropoxyphenyl)-1,3,4-oxadiazol-2-one ("Oxidazon");

pyridyloxyphenoxy derivatives: 2-[4'-(3'',5''-dichloropyridyl-2''-oxy)phenoxy]-propionic acid-(2-propinyl) ester;

phosphates: S-2-methylpiperidino-carbonylmethyl-O,O-dipropyl-phosphorodithioate ("Piperophos"); and pyrazoles: 1,3-dimethyl-4-(2',4'-dichlorobenzoyl)-5-(4'-tolylsulfonyloxy)-pyrazole.

An N-sulfonyl-imino-thiocarbonic acid diester of the formula I or a composition containing this antidote can be applied either before or after application of the herbicide, or it can be applied simultaneously with the herbicide. The treatment of the seed with a solution containing the antidote (seed dressing) has proved particularly efficient. The procedure is either to evaporate off the solvent and to apply the seed dry with an antidote coating around it, or to pre-soak the seed in an aqueous solution containing the antidote and to sow the seed in this condition, as is the customary practice in the case of rice.

The N-sulfonyl-imino-thiocarbonic acid diesters of the formula I are produced by reacting, in an aprotic dipolar solvent, a benzenesulfonamide of the formula II

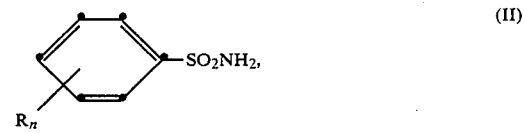

wherein R and n have the meanings given in the foregoing, in the presence of an alkali metal base, with carbon disulfide, and immediately further reacting the formed N-sulfonyl-imino-carbonic acid salt of the formula III

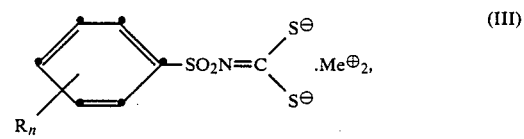

wherein R and n have the meanings defined in the foregoing, and Me is an alkali metal ion, with a halide or sulfate of the formula IV

wherein $R_1$ has the meaning defined in the foregoing, and Hal is a halogen atom, preferably chlorine, bromine or iodine, and Y is methyl or p-tolyl.

There is formed by this process, depending on the employed amount of starting compound of the formula IV, and after acidification, the N-sulfonyl-imino-mono- or dithiocarbonic acid ester of the formula Ia or Ib

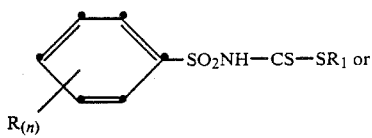

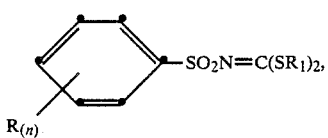

wherein R, R₁ and n have the meanings defined in the foregoing. Whereas the dithiocarbonic acid diester of the formula Ib is already the final product, the dithiocarbonic acid monoester of the formula Ia is reacted with an alcohol of the formula V $$R_2-OH \quad (V)$$

to give the thiocarbonic acid-O-ester of the formula VI

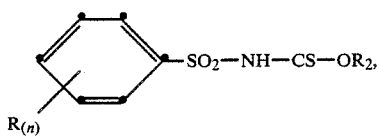

wherein R, R₂ and n have the meanings defined in the foregoing. This thiocarbonic acid-O-ester is subsequently treated, in the presence of a base, with a halide or sulfate of the formula IV given above, by which procedure is obtained a mixed dithiocarbonic acid-O,S-ester of the formula Ic

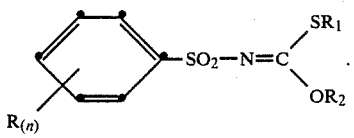

These reactions are known, and are described for example in Chem. Ber. 99 (1966) pp. 2885-2899.

Suitable aprotic dipolar solvents for the reaction of the sulfonamide with carbon disulfide are for example: dimethylformamide dimethyl sulfoxide, N-methylpyrrolidone and acetonitrile, in the solution of which the formed salt is preferably immediately further processed.

The reactions are performed at room temperature, or with cooling, since exothermic reactions frequently occur, which heat the mixture up to 50°-60° C.

The N-sulfonyl-imino-thiocarbonic acid diesters of the formula I according to the present invention can be used on their own or together with the herbicides to be antagonised.

The compounds of the formula I are used either in an unmodified form or preferably together with auxiliaries customarily employed in formulation practice, and are thus processed in a known manner for example into the form of emulsion concentrates, directly sprayable or dilutable solutions, diluted emulsions, wettable powders, soluble powders, dusts or granulates, and also encapsulations in for example polymeric substances. The application processes, such as spraying, atomising, dusting, scattering or pouring, and likewise the type of composition, are selected to suit the objectives to be achieved and the given conditions.

The formulations, that is to say, the compositions or preparations containing the active ingredient of the formula I and optionally a solid or liquid additive, are produced in a known manner, for example by the intimate mixing and/or grinding of the active ingredients with extenders, such as with solvents, solid carriers and optionally surface-active compounds (tensides).

Suitable solvents are: aromatic hydrocarbons, preferably the fractions $C_8$ to $C_{12}$, such as xylene mixtures or substituted naphthalenes, phthalic esters, such as dibutylor dioctylphthalate, aliphatic hydrocarbons, such as cyclohexane or paraffins, alcohols and glycols, as well as ethers and esters thereof, such as ethanol, ethylene glycol, ethylene glycol monomethyl or -ethyl ethers, ketones, such as cyclohexanone, strongly polar solvents, such as N-methyl-2-pyrrolidone, dimethyl sulfoxide or dimethylformamide, as well as optionally epoxidised vegetable oils, such as epoxidised coconut oil or soybean oil; or water.

The solid carriers used, for example for dusts and dispersible powders, are as a rule natural mineral fillers, such as calcite, talcum, kaolin, montmorillonite or attapulgite. In order to improve the physical properties, it is also possible to add highly dispersed silicic acid or highly dispersed absorbent polymers. Suitable granulated adsorptive carriers are porous types, for example pumice, ground brick, sepiolite or bentonite; and suitable nonsorbent carriers are materials such as calcite or sand. There can also be used a great number of pregranulated materials of inorganic or organic nature, such as in particular dolomite or ground plant residues.

Suitable surface-active compounds are, depending on the nature of the active ingredient of the formula I to be formulated, nonionic, cationic and/or anionic tensides having good emulsifying, dispersing and wetting properties. By 'tensides' are also meant mixtures of tensides.

Suitable anionic tensides are both so-called water-soluble soaps as well as water-soluble, synthetic, surface-active compounds.

Soaps which are applicable are the alkali metal, alkaline-earth metal or optionally substituted ammonium salts of higher fatty acids ($C_{10}$-$C_{22}$), for example the Na or K salts of oleic or stearic acid, or of natural fatty acid mixtures, which can be obtained for example from coconut oil or tallow oil. Also to be mentioned are the fatty acid-methyl-taurine salts.

So-called synthetic tensides are however more frequently used, particularly fatty sulfonates, fatty sulfates, sulfonated benzimidazole derivatives or alkylarylsulfonates. The fatty sulfonates or sulfates are as a rule in the form of alkali metal, alkaline-earth metal or optionally substituted ammonium salts, and contain an alkyl group having 8 to 22 C atoms, 'alkyl' including also the alkyl moiety of acyl groups, for example the Na or Ca salt of ligninsulfonic acid, of dodecylsulfuric acid ester or of a fatty alcohol sulfate mixture produced from natural fatty acids. Included amongst these are also the salts of sulfuric acid esters and sulfonic acids of fatty alcohol ethylene oxide adducts. The sulfonated benzimidazole derivatives preferably contain 2 sulfonic acids groups and a fatty acid group having 8-22 C atoms. Alkylarylsulfonates are for example the Na, Ca or triethanolamine salts of dodecylbenzenesulfonic acid, of dibutylnaphthalenesulfonic acid or of a naphthalenesulfonic acid-formaldehyde condensation product. Also suitable are corresponding phosphates, for example salts of the phosphoric ester of a p-nonylphenol-(4–14)-ethylene oxide adduct, and phospholipides.

Suitable nonionic tensides are in particular polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl moiety of the alkylphenols.

Further suitable nonionic tensides are the water-soluble polyethylene oxide adducts, which contain 20 to 250 ethylene glycol ether groups and 10 to 100 propylene glycol ether groups, with polypropylene glycol, ethylenediaminopolypropylene glycol and alkylpolypropylene glycol having 1 to 10 carbon atoms in the alkyl chain. The compounds mentioned usually contain 1 to 5 ethylene glycol units per propylene glycol unit. Examples of nonionic tensides which may be mentioned are: nonylphenol-polyethoxyethanols, castor oil polyglycol ethers, polypropylene/polyethyleneoxy adducts, tributylphenoxy-polyethoxyethanol, polyethylene glycol and octylphenoxy-polyethoxyethanol. Suitable also are fatty acid esters of polyoxyethylenesorbitan, such as polyoxyethylenesorbitan-trioleate.

In the case of the cationic tensides, they are in particular quaternary ammonium salts which contain as N-substituents at least one alkyl group having 8 to 22 C atoms and, as further substituents, lower, optionally halogenated alkyl, benzyl or lower hydroxyalkyl groups. The salts are preferably in the form of halides, methyl sulfates or ethyl sulfates, for example stearyltrimethylammonium chloride or benzyldi(2-chloroethyl)-ethylammonium bromide.

The tensides customarily used in formulation practice are described, inter alia, in the following publications:

"Mc Cutcheon's Detergents and Emulsifiers Annual", MC Publishing Corp., Ridgewood, N.J., 1979; M. and J. Ash, "Encyclopedia of Surfactants", Vol. I–III, Chemical Publishing Co., Inc. New York 1980–1981; H. Stache, "Tensid Taschenbuch", 2nd Edition, C. Hanser Verlag, Munich and Vienna, 1981.

The agrochemical preparations contain as a rule 0.1 to 99%, particularly 0.1 to 95%, of active ingredient of the formula I, 1 to 99% of a solid or liquid additive, and 0 to 25%, especially 0.1 to 25%, of a tenside.

Whereas commercial products are preferably in the form of concentrated compositions, the preparations employed by the end-user are as a rule diluted.

The compositions can also contain further additives such as stabilisers, antifoam agents, viscosity regulators, binders and adhesives, as well as fertilisers or other active substances for obtaining special effects.

Percentages and parts in the following Examples relate to weight.

EXAMPLE 1

Production of N-(4-chlorobenzenesulfonyl)-imino-thiocarbonic acid-O,S-dimethyl ester

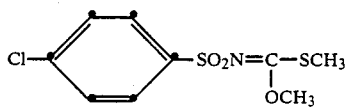

(a) N-4-(Chlorobenzenesulfonyl)-dithiocarbamic acid-S-methyl ester 384 g of 4-chlorobenzenesulfonamide (2 mols) are dissolved in 750 ml of dimethylformamide, and within 4 hours there are then added dropwise simultaneously, with stirring, 320 g of 50% aqueous sodium hydroxide solution (8 mols) and 152 g of carbon disulfide. The temperature is maintained by cooling at 10°–15° C., and the formed deep-red solution of the disodium salt is subsequently stirred for 2 hours at room temperature. A dropwise addition of 254 g of dimethyl sulfate (2 mols) is then made, the temperature being held at 15° C. by cooling. The mixture is afterwards stirred for 12 hours at room temperature and then diluted with water to 6 liters. The cloudy yellow solution is filtered through Celite and rendered acidic with concentrated hydrochloric acid. The N-(4-chlorobenzenesulfonyl)-dithiocarbamic acid-S-methyl ester precipitates in the form of oil and crystallises after a short time. After cooling and being washed with water, the compound is stirred up with a small amount of cold methanol to thus yield 270 g (48% of theory) of the above ester as a colourless crystalline powder, m.p. 135°–139° C. (decomp.).

(b) N-(4-Chlorobenzenesulfonyl)-thiocarbamic acid-O-methyl ester 14.1 g of N-(4-chlorophenylsulfonyl)-dithiocarbamic acid-S-methyl ester (0.05 mol) are refluxed in 100 ml of methanol, and after about 5 hours the formation of mercaptan has finished. The solvent is distilled off in a rotary evaporator, and the residue is recrystallised from methanol; yield 116 g (87% of theory), m.p. 129°–130° C.

(c) N-(4-Chlorobenzenesulfonyl)-imino-thiocarbonic acid-O,S-dimethyl ester 6.65 g of N-(4-chlorobenzenesulfonyl)-thiocarbamic acid-S-methyl ester (0.025 mol) are dissolved in 250 ml of dimethylformamide, and 2 g of 50% sodium hydroxide solution (0.025 mol) are added to the solution. There are then added dropwise, with cooling and stirring, 3.15 g of dimethyl sulfate (0.025 mol), and stirring is maintained at 30° C. for 2 hours. The mixture is then stirred into 300 ml of ice water, and the precipitate is filtered off. Recrystallisation from methanol yields 5.3 g (75% of theory) of the above mixed ester, m.p. 96°–97° C.

EXAMPLE 2

Production of N-(4-chlorobenzenesulfonyl)-imino-dithiocarbonic acid-S,S-dimethyl ester

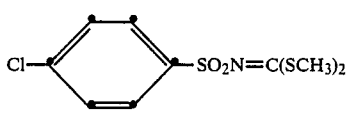

767 g of 4-chlorobenzenesulfonamide (4 mols) are dissolved in 1500 ml of dimethylformamide. There are then added dropwise simultaneously in the course of 5 hours, with stirring and cooling so that the temperature remains between 10° and 15° C., 640 g of 50% aqueous sodium hydroxide solution (8 mols) and 305 g of carbon disulfide (4 mols). The formed deep-red solution of the disodium salt is subsequently stirred for a further 2 hours at room temperature, and 100 g of dimethyl sulfate are then added dropwise, the temperature being held at 15° C. by cooling. The formed dispersion is afterwards stirred for 2 hours at 35° C., and is then diluted with 5 liters of water. A precipitate is formed and is filtered off. The yield after recrystallisation from methanol is 820 g (69% of theory) of N-(4-chlorobenzenesulfonyl)-imino-dithiocarbonic acid-S,S-dimethyl ester in the form of a colourless crystalline powder, m.p. 93°–94° C.

The compounds given in the following Table are produced in an analogous manner:

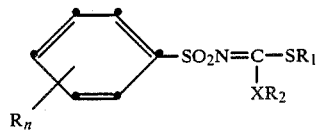

| Comp. No. | $R_n$ | $R_1$ | X | $R_2$ | Physical data m.p. °C. |
|---|---|---|---|---|---|
| 1 | H | $CH_3$ | S | $CH_3$ | m.p. 106–108° |
| 2 | H | $C_2H_5$ | S | $C_2H_5$ | m.p. 90° |
| 3 | 4-$CH_3$ | $CH_3$ | S | $CH_3$ | m.p. 108–110° |
| 4 | 4-$CH_3$ | $C_2H_5$ | S | $C_2H_5$ | m.p. 79° |
| 5 | 4-Cl | $CH_3$ | S | $CH_3$ | m.p. 94–95° Ex. 2 |
| 6 | 4-Cl | $C_2H_5$ | S | $C_2H_5$ | m.p. 51° |
| 7 | 4-Br | $CH_3$ | S | $CH_3$ | m.p. 109–112° |
| 8 | 4-Br | $C_2H_5$ | S | $C_2H_5$ | m.p. 66–68° |
| 9 | 4-$CH_3$ | $C_2H_5$ | S | $CH_2CH=CH_2$ | m.p. 61–64° |
| 10 | 4-$CH_3$ | $CH_3$ | S | $CH_2C\equiv CH$ | m.p. 113–115° |
| 11 | 4-$CF_3$ | $CH_3$ | S | $CH_3$ | |
| 12 | 4-$OCF_3$ | $CH_3$ | S | $CH_3$ | |
| 13 | 4-Cl | $CH_2-CH=CH_2$ | S | $CH_2-CH=CH_2$ | |
| 14 | 3,4 $Br_2$ | $CH_3$ | S | $CH_3$ | |
| 15 | 3,4 $Cl_2$ | $CH_3$ | S | $CH_3$ | |
| 16 | 3-Br, 4-Cl | $CH_3$ | S | $CH_3$ | |
| 17 | 4-Cl | $CH_3$ | O | $CH_3$ | m.p. 96–97 Ex. 1 |
| 18 | 4-Cl | $C_2H_4OCH_3$ | S | $C_2H_4OCH_3$ | |
| 19 | 4-$SCH_3$ | $CH_3$ | S | $CH_3$ | |
| 20 | 4-$OC_3H_7$—i | $CH_3$ | S | $CH_3$ | |
| 21 | 4-$OCHF_2$ | $CH_3$ | S | $CH_3$ | |
| 22 | 3-$CH_3$ | $CH_3$ | S | $CH_3$ | |
| 23 | 3-Cl | $CH_3$ | S | $CH_3$ | m.p. 83–85 |
| 24 | 3-F | $CH_3$ | S | $CH_3$ | |
| 25 | 4-F | $CH_3$ | S | $CH_3$ | m.p. 112–114 |
| 26 | 3-$CF_3$ | $CH_3$ | S | $CH_3$ | m.p. 53–56 |
| 27 | 4-Cl | $C_2H_5$ | O | $C_2H_5$ | |
| 28 | 4-Br | $CH_3$ | O | $CH_3$ | |
| 29 | 4-Br | $C_2H_5$ | O | $C_2H_5$ | |
| 30 | 4-$OCF_3$ | $CH_3$ | O | $CH_3$ | |
| 31 | 4-$CF_3$ | $CH_3$ | O | $CH_3$ | |
| 32 | 3,4 $Cl_2$ | $CH_3$ | O | $CH_3$ | |
| 33 | 3,4 $Br_2$ | $CH_3$ | O | $CH_3$ | |
| 34 | 4-Cl | $C_2H_4OCH_3$ | O | $CH_3$ | |
| 35 | 4-Cl | $CH_2CH=CH_2$ | O | $CH_3$ | oil |
| 36 | 3-Cl | $CH_2-COOCH_3$ | S | $CH_2COOCH_3$ | m.p. 64–65 |
| 37 | 4-Cl | $CH_2-COOCH_3$ | S | $CH_2COOCH_3$ | m.p. 93–94 |
| 38 | 3-$NO_2$ | $CH_3$ | S | $CH_3$ | m.p. 130–132 |
| 39 | 3,4 $Cl_2$ | $CH_3$ | S | $CH_3$ | m.p. 122–124 |
| 40 | 4-Cl | $CH_3$ | S | $CH_2CONH_2$ | m.p. 192–194 |
| 41 | 4-Cl | $CH_3$ | O | $C_3H_7iso$ | m.p. 53–56 |
| 42 | 4-Cl | $CH_3$ | S | $CH_2COOCH_3$ | 125–127 |
| 43 | 4-Cl | $CH_3$ | S | benzyl | 95–98 |
| 44 | 4-Cl | phenyl | O | $CH_3$ | 75–88 |
| 45 | 4-Cl | $CH_2C\equiv CH$ | O | $CH_3$ | 91–95 |
| 46 | 4-Cl | $CH_3$ | O | phenyl | 127–129 |
| 47 | 4-Cl | $CH_3$ | S | phenyl | 130–132 |
| 48 | 4-Cl | $CH_3$ | S | H | 139–141 |
| 49 | 4-Br | 4-fluorobenzyl | S | 4-fluorobenzyl | 120–125 |
| 50 | 4-Br | $CH_3$ | S | 4-fluorobenzyl | 108–110 |
| 51 | 4-Br | $CH_3$ | S | H | 135–137 |
| 52 | 4-Cl | 4-chlorobenzyl | S | 4-chlorobenzyl | 123–125 |
| 53 | 4-$CH_3$ | $CH_3$ | S | $CH_2COOCH_3$ | 99–101 |
| 54 | 4-Br, 3-Cl | $CH_3$ | S | $CH_3$ | 115–121 |
| 55 | 4-Br, 3-$CH_3$ | $CH_3$ | S | $CH_3$ | 110–112 |
| 56 | 3-Cl, 4-$CF_3$ | $CH_3$ | S | $CH_3$ | 113–115 |
| 57 | 3,4 $Br_2$ | $CH_3$ | S | $CH_3$ | 104–106 |
| 58 | 4-$COOCH_3$ | $CH_3$ | S | $CH_3$ | |
| 59 | 4-$COOC_2H_5$ | $CH_3$ | S | $CH_3$ | |
| 60 | 4-COOH | $CH_3$ | S | $CH_3$ | |
| 61 | 3,4 $F_2$ | $CH_3$ | S | $CH_3$ | |
| 62 | 4-Cl | $CH_3$ | S | $CH_3$ | 94–95 |
| 63 | 4-$iC_3H_7$ | $CH_3$ | S | $CH_3$ | 97–99 |
| 64 | 4-Cl,2,5($OCH_3)_2$ | $CH_3$ | S | $CH_3$ | 169–171 |
| 65 | 4-$(C_2H_5OCO)_2C=CHNH$— | $CH_3$ | S | $CH_3$ | 138–142 |
| 66 | 2-$CH_3$, 4-Cl | $CH_3$ | S | $CH_3$ | 121–123 |

-continued

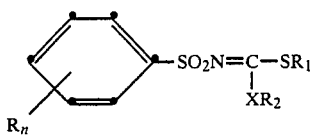

| Comp. No. | $R_n$ | $R_1$ | X | $R_2$ | Physical data m.p. °C. |
|---|---|---|---|---|---|
| 67 | 2,3-OC$_2$H$_4$ | CH$_3$ | S | CH$_3$ | 161–163 |
| 68 | 2-CH$_3$, 3-Cl | CH$_3$ | S | CH$_3$ | 138–141 |
| 69 | 3-Cl, 4-CH$_3$ | CH$_3$ | S | CH$_3$ | 121–122 |
| 70 | 4-(iC$_3$H$_7$)$_2$NCO— | CH$_3$ | S | CH$_3$ | 174–176 |
| 71 | 3,4 Br$_2$ | CH$_3$ | S | CH$_3$ | 104–106 |
| 72 | 3-Cl, 4-Br | CH$_3$ | S | CH$_3$ | 115–121 |
| 73 | 3-CF$_3$, 4-Cl | CH$_3$ | S | CH$_3$ | 113–115 |
| 74 | 3-CH$_3$, 4-Br | CH$_3$ | S | CH$_3$ | 110–112 |
| 75 | 3,4-CH=CH—CH=CH— | CH$_3$ | S | CH$_3$ | 105–106 |
| 76 | 4-CH$_3$CONH— | CH$_3$ | S | CH$_3$ | 176–177 |
| 77 | 4-(CH$_3$)$_2$NCONH—2-CH$_3$ | CH$_3$ | S | CH$_3$ | 206–207 |
| 78 | 4-CH$_3$ | CH$_3$ | S | 4,5-dihydrothien-2-yl | 144–146 |
| 79 | 4-CH$_3$ | CH$_3$ | S | 1-methyl-imidazol-2-yl | 190–192 |
| 80 | 4-CH$_3$ | CH$_3$ | S | 1,2,4-triazol-3-yl | 163–165 |
| 81 | 4-CH$_3$ | CH$_3$ | S | pyrid-2-yl | 171–173 |
| 82 | 4-CH$_3$ | CH$_3$ | S | piperid-2-yl | 144–146 |
| 83 | 4-CH$_3$ | CH$_3$ | S | 4,6-dimethyl-piperid-2-yl | 122–124 |
| 84 | 4-CH$_3$ | CH$_3$ | S | benzoxazol-2-yl | 130–131 |
| 85 | 4-CH$_3$ | CH$_3$ | S | benzthiazol-2-yl | 152–153 |
| 86 | 4-C$_2$H$_5$ | CH$_3$ | S | CH$_3$ | |
| 87 | 4-C$_2$H$_5$ | CH$_3$ | O | CH$_3$ | |
| 88 | 4-n C$_4$H$_9$ | CH$_3$ | O | CH$_3$ | |
| 89 | 4-s C$_4$H$_9$ | CH$_3$ | S | CH$_3$ | |
| 90 | 4-i.C$_4$H$_9$ | CH$_3$ | O | CH$_3$ | |
| 91 | 4-t.C$_4$H$_9$ | CH$_3$ | S | CH$_3$ | |
| 92 | 4-CH$_2$=CHCH$_2$ | CH$_3$ | S | CH$_3$ | |
| 93 | 2-CH$_2$=CH—CH$_2$ | CH$_3$ | S | CH$_3$ | |
| 94 | 4-C$_6$H$_5$ | CH$_3$ | S | CH$_3$ | |
| 95 | 4-C$_6$H$_5$—CH$_2$ | CH$_3$ | S | CH$_3$ | |
| 96 | 4-CF$_3$ | CH$_3$ | S | CH$_3$ | |
| 97 | 4-CH$_3$O | CH$_3$ | S | CH$_3$ | |
| 98 | 3-Cl, 4-CH$_3$O | CH$_3$ | S | CH$_3$ | |
| 99 | 2-Cl, 4-CH$_3$O | CH$_3$ | S | CH$_3$ | |
| 100 | 4-CH$_2$=CHCH$_2$O | CH$_3$ | S | CH$_3$ | |
| 101 | 4-CH≡CCH$_2$O | CH$_3$ | S | CH$_3$ | |
| 102 | 4-CH$_2$=CCl—CH$_2$O | CH$_3$ | S | CH$_3$ | |
| 103 | 2-CH$_2$=CH—CH$_2$O | CH$_3$ | S | CH$_3$ | |
| 104 | 4-CH$_2$=CH—CH$_2$O | CH$_3$ | O | CH$_3$ | |
| 105 | 4-(4-Cl—C$_6$H$_4$)—CH$_2$O | CH$_3$ | S | CH$_3$ | |
| 106 | 4-(2',4'-Cl$_2$—C$_6$H$_3$)CH$_2$O | CH$_3$ | S | CH$_3$ | |
| 107 | 4-C$_6$H$_5$—CH$_2$O | CH$_3$ | O | CH$_3$ | |
| 108 | 4-C$_6$H$_5$O | CH$_3$ | S | CH$_3$ | |
| 109 | 4-C$_6$H$_5$O | CH$_3$ | O | CH$_3$ | |
| 110 | 4-(4'-Cl—C$_6$H$_4$)O | CH$_3$ | S | CH$_3$ | |
| 111 | 4-(4'-NO$_2$C$_6$H$_4$)O | CH$_3$ | S | CH$_3$ | |
| 112 | 4-(4'-CF$_3$—C$_6$H$_4$)O | CH$_3$ | S | CH$_3$ | |
| 113 | 4-CH$_3$O—C$_2$H$_4$O | CH$_3$ | S | CH$_3$ | |
| 114 | 4-CH$_3$O—C$_2$H$_4$O | CH$_3$ | O | CH$_3$ | |
| 115 | 4-CHF$_2$O | CH$_3$ | S | CH$_3$ | |
| 116 | 4-CF$_3$O | CH$_3$ | S | CH$_3$ | |
| 117 | 4-CH$_3$S | CH$_3$ | S | CH$_3$ | |
| 118 | 4-CH$_3$SO$_2$ | CH$_3$ | S | CH$_3$ | |
| 119 | 4-CH$_3$OCOCH$_2$ | CH$_3$ | S | CH$_3$ | |
| 120 | 4-NC—CH$_2$ | CH$_3$ | S | CH$_3$ | |
| 121 | 4-(CH$_3$)$_2$—NCOCH$_2$ | CH$_3$ | S | CH$_3$ | |
| 122 | 2-NC—CH$_2$ | CH$_3$ | S | CH$_3$ | |
| 123 | 4-(CH$_3$)$_2$NSO$_2$ | CH$_3$ | S | CH$_3$ | |
| 124 | 4-(4'-Cl—C$_6$H$_4$)S | CH$_3$ | S | CH$_3$ | |
| 125 | 4-(4'-Cl—C$_6$H$_4$)SO$_2$ | CH$_3$ | S | CH$_3$ | |
| 126 | 4-CH$_3$ | CH$_3$ | S | furan-2-yl | |
| 127 | 4-CH$_3$ | CH$_3$ | S | 4,5-dihydrofuran-2-yl | |
| 128 | 4-Cl | CH$_3$ | S | thien-2-yl | |
| 129 | 4-Cl | CH$_3$ | S | 4,5-dihydrothien-2-yl | |
| 130 | 4-Cl | CH$_3$ | S | pyrrol-2-yl | |
| 131 | 4-CH$_3$ | CH$_3$ | S | 1-methylpyrrol-2-yl | |
| 132 | 4-Cl | CH$_3$ | S | pyrid-3-yl | |
| 133 | 4-CH$_3$ | CH$_3$ | S | benzyl | |
| 134 | 4-CH$_3$ | CH$_3$ | S | 4-chlorobenzyl | |
| 135 | 4-Cl | CH$_3$ | S | phenyl | |
| 136 | 4-Cl | CH$_3$ | S | 4-chlorophenyl | |
| 137 | 4-Cl | CH$_3$ | S | CH$_2$C≡CH | |
| 138 | 4-Cl | CH$_2$C≡CH | S | CH$_2$C≡CH | |

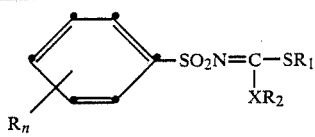

| Comp. No. | $R_n$ | $R_1$ | X | $R_2$ | Physical data m.p. °C. |
|---|---|---|---|---|---|
| 139 | 4-$CH_3$ | $CH_3$ | S | $CH_2C\equiv CH$ | |
| 140 | 4-$CH_3$ | $CH_2C\equiv CH$ | S | $CH_2C\equiv CH$ | |

Formulation Examples

The compounds of the formula I are generally not used as such in agriculture but are incorporated into ready-for-use compositions which can be applied either directly or diluted with water.

EXAMPLE 3

Dusts

The following substances are used to produce (a) a 5% dust and (b) a 2% dust:

(a)
- 5 parts of N-(4-chlorobenzenesulfonyl)-imino-dithiocarbonic acid dimethyl ester, or a mixture thereof with 2-chloro-2',6'-diethyl-N-(butoxymethyl)-acetanilide, and
- 95 parts of talcum; and (b)
- 2 parts of the above active ingredient or of a mixture thereof as above,
- 1 part of highly dispersed silicic acid, and
- 97 parts of talcum.

The active ingredients are mixed and ground with the carriers, and can be applied in this form by dusting.

EXAMPLE 4

Granulate

The following substances are used to produce a 5% granulate:
- 5 parts of N-(benzenesulfonyl)-imino-dithiocarbonic acid dimethyl ester, or of a mixture thereof with 2-chloro-2',6'-diethyl-N-(methoxymethyl)-acetanilide,
- 0.25 part of epoxidised vegetable oil,
- 0.25 part of cetyl polyglycol ether,
- 3.50 parts of polyethylene glycol, and
- 91 parts of kaolin (particle size 0.3–0.8 mm).

The active ingredient or the mixture is mixed with the vegetable oil, and the mixture obtained is dissolved in 6 parts of acetone, after which the polyethylene glycol and the cetyl polyglycol ether are added. The resulting solution is sprayed onto kaolin, and the acetone is subsequently evaporated off in vacuo. A microgranulate of this type is advantageously worked into seed furrows.

EXAMPLE 5

Wettable powders

The following constituents are used to produce wettable powders containing (a) 70%, (b) 40%, (c) 25%, (d) 25% and (e) 10% of active ingredient:

(a)
- 70 parts of N-(4-chlorobenzenesulfonyl)-imino-thiocarbonic acid, O,S-dimethyl ester, or of a mixture thereof with 2-chloro-2',6'-diethyl-N-(2''-propoxyethyl)-acetanilide,
- 5 parts of sodium dibutylnaphthalene sulfonate,
- 3 parts of naphthalenesulfonic acid/phenolsulfonic acid/formaldehyde condensate 3:2:1,
- 10 parts of kaolin, and
- 12 parts of Champagne chalk;

(b)
- 40 parts of active ingredient or of a mixture as above,
- 5 parts of sodium lignin sulfonate,
- 1 part of sodium dibutylnaphthalene sulfonate, and
- 54 parts of silicic acid.

(c)
- 25 parts of active ingredient or of a mixture as above,
- 4.5 parts of calcium lignin sulfonate,
- 1.9 parts of Champagne chalk/hydroxyethyl cellulose mixture (1:1),
- 1.5 parts of sodium dibutylnaphthalene sulfonate,
- 19.5 parts of silicic acid,
- 19.5 parts of Champagne chalk, and
- 28.1 parts of kaolin;

(d)
- 25 parts of active ingredient or of a mixture as above,
- 2.5 parts of isooctylphenoxy-polyoxyethylene-ethanol,
- 1.7 parts of Champagne chalk/hydroxyethyl cellulose mixture (1:1),
- 8.3 parts of sodium aluminium silicate,
- 16.5 parts of kieselguhr, and
- 46 parts of kaolin; and (e)
- 10 parts of active ingredient or of a mixture as above,
- 3 parts of a mixture of the sodium salts of saturated fatty alcohol sulfates,
- 5 parts of naphthalenesulfonic acid/formaldehyde condensate, and
- 82 parts of kaolin.

The active ingredients are intimately mixed in suitable mixers with the additives, and the mixture is ground in appropriate mills and rollers. Wettable powders having excellent wetting and suspension properties are obtained. These wettable powders can be diluted with water to give suspensions of the concentration required, and in this form they are suitable in particular for leaf application.

EXAMPLE 6

Emulsifiable concentrate

The following substances are used to produce a 25% emulsifiable concentrate:
- 25 parts of N-(4-tolylsulfonyl)-imino-dithiocarbonic acid dimethyl ester or a mixture thereof with 2-chloro-6'-ethyl-N-(2'''-methoxy-1'''-methylethyl)-aceto-toluidide,
- 10 parts of an alkylarylsulfonate/fatty alcohol polyglycol ether mixture, 5 parts of dimethylformamide, and
57 parts of xylene.

EXAMPLE 7
Pastes

The following substances are used to produce as 45% paste:

(a)
- 45 parts of N-(benzenesulfonyl)-imino-thiocarbonic acid-O,S-dimethyl ester, or a mixture thereof with 2-chloro-2',6'-diethyl-N-(methoxymethyl)-acetanilide,
- 5 parts of sodium aluminium silicate,
- 14 parts of cetyl polyethylene glycol ether having 8 mols of ethylene oxide,
- 1 part of oleyl polyethylene glycol ether having 5 mols of ethylene oxide,
- 2 parts of spindle oil,
- 23 parts of water, and
- 10 parts of polyethylene glycol; and (b)
- 45 parts of the above active ingredient or of the mixture thereof as above,
- 5 parts of ethylene glycol,
- 3 parts of octylphenoxypolyethylene glycol having 9–10 mols of ethylene oxide per mol of octylphenol,
- 3 parts of a mixture of aromatic sulfonic acids, condensed with formaldehyde as ammonium salt,
- 1 part of silicone oil in the form of a 75% emulsion,
- 0.1 part of a mixture of 1(3-chloroallyl)-3,5,7-triazoazonium-adamantane chloride with sodium carbonate, chloride value at least 11.5%, 0.2 part of a biopolymeric thickener having a maximum of 100 nuclei per gram, and 42.7 parts of water.

The active ingredient is intimately mixed and ground with the additives in suitable devices. There is obtained a paste from which suspensions of the concentration required can be produced by dilution with water.

Biological Example

The capability of the compounds of the formula I to protect rice crops against the phytotoxic action of strong herbicides can be seen from the following Example. In the test descriptions, the compounds of the formula I are designated as antidotes. The relative protective action is given in %. The value 0% denotes the action of the herbicide when applied on its own; 100% signifies the desired normal growth of the cultivated plant.

EXAMPLE 8

Test with antidote and herbicide on rice sown in water. Application of the antidote during soaking of the rice seeds Rice seeds are soaked during 48 hours in solutions of 100 ppm of the substance to be tested as antidote. The seeds are subsequently left to dry for about 2 hours until they are no longer sticky. Plastics containers (8 cm in width and 10 cm in height) are filled with sandy loam to within 2 cm of the top edge. The pre-soaked seeds are sown on the surface of the soil in each container, and are covered over with a small amount of soil. The soil is kept in a moist (not boggy) condition, and the herbicide is sprayed as a dilute solution onto the surface of the soil. The level of water is successively raised to correspond to the growth of the plants. The relative protective action of the antidote is estimated in percent 21 days after sowing. Reference values are provided by the plants treated with the herbicide alone (no protective action), and by the completely untreated control plants (100% growth). The results are summarised in the Table which follows:

The herbicide used in 2-chloro-2',6'-diethyl-N-(2"-propyloxyethyl)-acetanilide ("Pretilachlor"), and the amount applied corresponds to 0.25 kg per hectare.

| Compound No. | Relative protective action in % |
| --- | --- |
| 1 | 38 |
| 3 | 75 |
| 5 | 50 |
| 7 | 63 |
| 8 | 25 |
| 23 | 63 |
| 25 | 12 |
| 35 | 25 |
| 39 | 75 |
| 40 | 12.5 |
| 41 | 25 |
| 45 | 50 |
| 47 | 12.5 |

EXAMPLE 9

Test with antidote and herbicide on rice. Application of antidote and herbicide as tank mixture in the pre-emergence process Rice seeds are pre-soaked for 48 hours in water. Plastics containers (25 cm long, 17 cm wide and 12 cm high) are filled with soil, into which the pre-soaked seeds are are sown. The substances to be tested as antidote together with the herbicide is then sprayed as a tank mixture onto the soil. The level of the water is successively raised to correspond to the growth of the rice plants. The protective action of the antidote is estimated in percent 18 days after sowing. Reference values are provided by the plants treated with the herbicide alone (no protective action), and by the completely untreated plants (100% growth). The results are summarised below.

| Herbicide: 2-Chloro-2',6'-diethyl-N—(2"-propyloxyethyl)-acetanilide ("Pretilachlor"): applied amount 0.5 kg/ha. | | |
| --- | --- | --- |
| Compound No. | Applied amount in kg/ha | Relative protective action |
| 3 | 0.5 | 38 |
| 5 | 0.5 | 50 |
| 7 | 0.5 | 50 |
| 23 | 0.5 | 63 |
| 39 | 0.5 | 75 |
| 45 | 0.5 | 38 |

EXAMPLE 10

Test with antidote and herbicide on transplanted rice; application method: tank mixture Rice plants are grown to the 1½-2-leaf stage in soil. The plants are then transplanted in bunches (always 3 plants together) into sandy loam in containers (47 cm long, 29 cm wide and 24 cm high). The surface of the soil is subsequently covered with water to a depth of 1.5-2 cm. Two to three days after transplantation, the herbicide together with the substance to be tested as antidote is applied directly as a tank mixture into the water. The protective action of the antidote is estimated in percent 24 days after transplantation. Reference values are provided by the plants treated with the herbicide alone (no protective action), and by the completely untreated control plants (100% growth). The results are summarised below.

| Compound No. | Applied amount kg/ha | Applied amount of herbicide kg/ha | Relative protective action % |
|---|---|---|---|
| Herbicide: 2-Chloro-2',6'-diethyl-N—(2''-propyloxyethyl)-acetanilide ("Pretilachlor") | | | |
| 3 | 1 | 1 | 12.5 |
| 3 | 0.75 | 0.75 | 12.5 |
| 5 | 1 | 1 | 38 |
| 5 | 0.75 | 0.75 | 25 |
| 7 | 1 | 1 | 25 |
| 7 | 0.75 | 0.75 | 25 |

EXAMPLE 11

Test with antidote and herbicide on dry-sown rice. Application of the antidote as seed dressing Rice seeds are mixed with the substance to be used as antidote in a glass container. Seeds and product are well mixed together by shaking and rotation. Containers (47 cm long, 29 cm wide and 24 cm high) are then filled with sandy loam, and the dressed seeds are sown therein. After the seeds have been covered, the herbicide in dilute solution is sprayed onto the surface of the soil. About 20 days after sowing (3-leaf stage of the rice plants), the surface of the soil is covered to a depth of 4 cm with water. Thirty days after application of the herbicide, the protective action of the antidote is estimated in percent. Reference values are provided by plants treated with the herbicide alone (no protective action), and also by the completely untreated control plants (100% growth).

The results are summarised below.

| Compound No. | Applied amount g/kg of seed | Applied amount of herbicide kg/ha | Relative protective action % |
|---|---|---|---|
| Herbicide: 2-Chloro-2',6'-diethyl-N—(2''-propyloxyethyl)-acetanilide ("Pretilachlor") | | | |
| 7 | 2 | 1 | 25 |
| 7 | 2 | 2 | 75 |
| 7 | 2 | 3 | 38 |
| Herbicide: S-Ethyl-N,N—hexamethylenethiocarbamate ("Ordram") | | | |
| 5 | 2 | 2 | 38 |
| 7 | 2 | 4 | 50 |
| Herbicide: S—4-Chlorobenzyl-N,N—diethylthiocarbamate ("Thiobencarb") | | | |
| 7 | 2 | 4 | 25 |
| Herbicide: 2-Chloro-6'-ethyl-N—(2''-methoxy-1''-methylethyl)-acet-o-toluidide ("Metolachlor") | | | |
| 3 | 4 | 0.5 | 25 |
| 5 | 2 | 0.25 | 25 |

EXAMPLE 12

Test with antidote and herbicide on rice sown dry. The antidote is applied as a seed dressing Rice seeds of the IR-36 variety are mixed together in a glass container with the substance to be tested as safener (antidote), and seeds and product are thoroughly mixed by shaking and rotation. Plastics containers (47 cm long, 29 cm wide and 24 cm high) are then filled with sandy loam, and the dressed seeds are sown therein. After the seeds have been covered over, the herbicide is sprayed onto the surface of the soil. Eighteen days after sowing, the protective action of the safener is estimated in percent. The plants treated with the herbicide alone (no protective action) and the completely untreated control plants (100% growth) provide reference values. The results are as follows:

| Compound No. | Applied amount g/kg of seed | Applied amount of herbicide kg/ha | Relative protective action % |
|---|---|---|---|
| Herbicide: 2-Chloro-2',6'-diethyl-N—(2''-propyloxyethyl)-acetanilide ("Pretilachlor") | | | |
| 7 | 2 | 1 | 25 |
| 7 | 2 | 2 | 75 |
| 7 | 2 | 3 | 38 |
| Herbicide: S—Ethyl-N,N—hexamethylenethiocarbamate ("Ordram") | | | |
| 5 | 2 | 2 | 38 |
| 7 | 2 | 4 | 50 |
| Herbicide: S—4-Chlorobenzyl-N,N—diethylthiocarbamate ("Thiobencarb") | | | |
| 7 | 2 | 4 | 25 |
| Herbicide: 2-Chloro-6'-ethyl-N—(2''-methoxy-1''-methylethyl)-acet-o-toluidide ("Metolachlor") | | | |
| 3 | 4 | 0.25 | 25 |
| 5 | 2 | 0.25 | 25 |

EXAMPLE 13

Test with antidote and herbicide on dry-sown and later flooded rice. Application of herbicide and antidote as tank mixture in the pre-emergence process Rice seeds of the IR-36 variety are sown in containers (47 cm long, 29 cm wide and 24 cm high), covered over and lightly pressed down. The substance to be tested as antidote with the herbicide is then sprayed, as a tank mixture, onto the surface of the soil. About 20 days after sowing (3-leaf stage of the rice plants), the soil surface is covered with water to a depth of 4 cm, and 30 days after application, the protective action of the antidote is estimated in percent. The plants treated with the herbicide alone (no protective action) and the completely untreated control plants (100% growth) provide reference values.

The results are summarised in the following Table.

| Compound No. | Applied amount kg/ha | Applied amount of herbicide kg/ha | Relative protective action % |
|---|---|---|---|
| Herbicide: 2-Chloro-2',6'-diethyl-N—(2''-propyloxyethyl)-acetanilide ("Pretilachlor") | | | |
| 7 | 3 | 3 | 63 |
| 7 | 2 | 2 | 75 |
| 7 | 1.5 | 1.5 | 63 |

What is claimed is:

1. A composition for the reduction of phytotoxic action of haloacetamide and thiocarbamate herbicides on rice crops which comprises an antidotally effective amount of a compound of the formula:

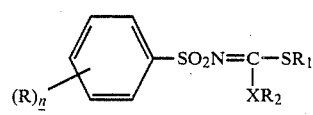

wherein
n has a value of from 0 to 3;
R is halo, cyano, nitro, alkyl of 1 to 4 carbon atoms, haloalkyl of 1 to 4 carbon atoms, alkoxy of 1 to 4 carbon atoms, haloalkoxy of 1 to 4 carbon atoms, alkylthio of 1 to 4 carbon atoms, alkylsulfonyl of 1 to 4 carbon atoms, sulfamoyl, dialkylsulfamoyl in which each alkyl group is of 1 to 4 carbon atoms or —COOR$_3$;
each of R$_1$ and R$_2$, independently of the other is alkyl of 1 to 4 carbon atoms, alkoxyalkyl of 2 to 5 carbon atoms, haloalkyl of 1 to 4 carbon atoms, carbalkoxymethyl wherein alkoxy is of 1 to 4 carbon atoms, carbamoylmethyl, alkenyl of of 3 to 6 carbon atoms, haloalkenyl of 3 to 6 carbon atoms, alkynyl of 3 to 6 carbon atoms, phenyl, benzyl or halobenzyl; R$_3$ is alkyl of 1 to 4 carbon atoms, alkenyl of 3 to 6 carbon atoms, alkynyl of 3 to 6 carbon atoms or cycloalkenyl of 3 to 6 carbon atoms, each of which is unsubstituted or substituted with halo, cyano, or nitro; and
X is O or S,
in combination with an inert carrier.

2. A composition according to claim 1 wherein in said compound n is 1 or 2.

3. A composition according to claim 2 wherein when in said compound n is 1, R is in the 3- or 4-position relative to the sulfonyl group or when R is 2, one R is in the 3-position and the second R is in the 4-position relative to the sulfonyl group.

4. A composition according to claim 3 wherein in said compound R is methyl, chloro, bromo, fluoro or nitro.

5. A composition according to claim 4 wherein in said compound each of R$_1$ and R$_2$ independently of the other is methyl, ethyl, propyl, carbomethoxymethyl, methoxyethyl, carbamoylmethyl, allyl, propargyl, phenyl, benzyl, chlorobenzyl or fluorobenzyl.

6. A composition according to claim 1 wherein a haloacetamide or thiocarbamate herbicide is admixed with said compound.

7. A composition according to claim 1 wherein said compound R$_1$ and R$_2$ are each methyl.

8. A composition according to claim 1 wherein said compound is N-(4-chlorobenzenesulfonyl)-imino-dithiocarbonic acid dimethyl ester.

9. A composition according to claim 1 wherein said compound is N-(4-bromobenzenesulfonyl)-imino-dithiocarbonic acid dimethyl ester.

10. A composition according to claim 1 wherein said compound is N-(3,4-dichlorobenzenesulfonyl)-iminodithiocarbonic acid dimethyl ester.

11. A composition according to claim 1 wherein said compound is N-(3-chlorobenzenesulfonyl)-iminodithiocarbonic acid dimethyl ester.

12. A composition according to claim 1 wherein said compound is N-(4-methylbenzenesulfonyl)-iminodithiocarbonic acid dimethyl ester.

13. A composition according to claim 1 wherein said compound is N-(3-nitrobenzenesulfonyl)-iminodithiocarbonic acid dimethyl ester.

14. A composition according to claim 1 wherein said compound is N-(4-chlorobenzenesulfonyl)-iminodithiocarbonic acid O-methyl-S-propynyl diester.

15. The method of reducing the phytotoxic effects of haloacetamide and thiocarbamate herbicides on rice crops which comprises applying an antidotally effective amount of a compound of the formula:

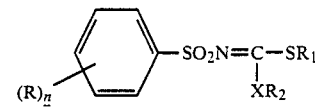

wherein
n has a value of from 0 to 3;
R is halo, cyano, nitro, alkyl of 1 to 4 carbon atoms, haloalkyl of 1 to 4 carbon atoms, alkoxy of 1 to 4 carbon atoms, haloalkoxy of 1 to 4 carbon atoms, alkylthio of 1 to 4 carbon atoms, alkylsulfonyl of 1 to 4 carbon atoms, sulfamoyl, dialkylsulfamoyl in which each alkyl group is of 1 to 4 carbon atoms or —COOR$_3$;
each of R$_1$ and R$_2$, independently of the other is alkyl of 1 to 4 carbon atoms, alkoxyalkyl of 2 to 5 carbon atoms, haloalkyl of 1 to 4 carbon atoms, carbalkoxymethyl wherein alkoxy is of 1 to 4 carbon atoms, carbamoylmethyl, alkenyl of of 3 to 6 carbon atoms, haloalkenyl of 3 to 6 carbon atoms, alkynyl of 3 to 6 carbon atoms, phenyl, benzyl or halobenzyl; R$_3$ is alkyl of 1 to 4 carbon atoms, alkenyl of 3 to 6 carbon atoms, alkynyl of 3 to 6 carbon atoms or cycloalkenyl of 3 to 6 carbon atoms, each of which is unsubstituted or substituted with halo, cyano, or nitro; and
X is O or S,
to the seeds, plants or environs of the rice crop.

16. The method of claim 15 wherein the seeds of the rice crop are treated before application of said herbicide.

17. The method of claim 15 wherein the rice plants or their environs are treated before or during the application of said herbicide.

18. The method of claim 15 wherein in said compound
n is 1 or 2;
R is methyl, chloro, bromo, or fluoro, and when n is 1, R is in the 3- or 4-position or when n is 2, one R is in the 3-position and the second R is in the 4-position, all relative to the depicted sulfonyl group; and
each of R$_1$ and R$_2$, independently of the other, is methyl, ethyl, propyl, carbomethoxymethyl, methoxyethyl, carbamoylmethyl, allyl, propargyl, phenyl, benzyl, chlorobenzyl or fluorobenzyl.

19. The method according to claim 15 wherein said compound is N-(4-chlorobenzenesulfonyl)-imino-dithiocarbonic acid dimethyl ester.

20. The method according to claim 15 wherein said compound is N-(4-bromobenzenesulfonyl)-imino-dithiocarbonic acid dimethyl ester.

21. The method according to claim 15 wherein said compound is N-(3,4-dichlorobenzenesulfonyl)-iminodithiocarbonic acid dimethyl ester.

22. The method according to claim 15 wherein said compound is N-(3-chlorobenzenesulfonyl)-iminodithiocarbonic acid dimethyl ester.

23. The method according to claim 15 wherein said compound is N-(4-methylbenzenesulfonyl)-iminodithiocarbonic acid dimethyl ester.

24. The method according to claim 15 wherein said compound is N-(3-nitrobenzenesulfonyl)-iminodithiocarbonic acid dimethyl ester.

25. The method according to claim 15 wherein said compound is N-(4-chlorobenzenesulfonyl)-iminodithiocarbonic acid O-methyl-S-propynyl diester.

* * * * *